United States Patent [19]
Bargiotti et al.

[11] Patent Number: 4,522,815
[45] Date of Patent: Jun. 11, 1985

[54] ANTHRACYCLINE GLYCOSIDES

[75] Inventors: Alberto Bargiotti; Sergio Penco; Anna M. Casazza, all of Milan, Italy

[73] Assignee: Farmitalia Carlo Erba S.p.A., Italy

[21] Appl. No.: 499,308

[22] Filed: May 31, 1983

[30] Foreign Application Priority Data

May 24, 1982 [GB] United Kingdom ............... 8215083

[51] Int. Cl.³ ..................... A61K 31/71; C07H 15/24
[52] U.S. Cl. ...................................... 514/34; 536/6.4; 260/365
[58] Field of Search .................... 536/6.4; 424/180

[56] References Cited

U.S. PATENT DOCUMENTS

| | | | |
|---|---|---|---|
| 4,067,969 | 1/1978 | Penco et al. | 536/6.4 |
| 4,201,773 | 5/1980 | Horton et al. | 536/6.4 |
| 4,302,449 | 11/1981 | El Khadem et al. | 536/6.4 |
| 4,348,388 | 9/1982 | Garland et al. | 536/6.4 |

Primary Examiner—Johnnie R. Brown
Assistant Examiner—Elli Peselev
Attorney, Agent, or Firm—Sheldon Palmer

[57] ABSTRACT

Disclosed is a process for preparing the glycoside antitumor anthracyclines 7-0-(2,6-dideoxy-α-L-arabino-hexopyranosyl)-daunomycinone (Ia); 4-demethoxy-7-0-(2,6-dideoxy-α-L-arabino-hexopyranosyl)-daunomycinone (Ib); 7-0-(2,6-dideoxy-α-L-arabino-hexopyranosyl)-adriamycinone (Ic); 4-demethoxy-7-0-(2,6-dideoxy-α-L-arabino-hexopyranosyl)-adriamycinone (Id); 7-0-(2,3,6-trideoxy-α-L-erythro-hex-2-enopyranosyl)-daunomycinone (IIa); 4-demethoxy-7-0-(2,3,6-trideoxy-α-L-erythro-hex-2-enopyranosyl)-daunomycinone (IIb); 7-0-(2,3,6-trideoxy-α-L-erythro-hex-2-enopyranosyl)-adriamycinone (IIc); and 4-demethoxy-7-0-(2,3,6-trideoxy-α-L-erythro-hex-2-enopyranosyl)-adriamycinone (IId). Compounds Ia, Ib, IIa, IIb are prepared by condensing daunomycinone and 4-demethoxydaunomycinone with 3,4-di-0-acetyl-2,6-dideoxy-α-L-arabino-hexopyranosyl chloride in an inert solvent in the presence of silver triflate (silver trifluoromethansulfonate), as catalyst, and by removing the protecting groups. Analogously the derivatives Ic, Id, IIc and IId are prepared by condensing a novel reactive protected derivative of adriamycinone and 4-demethoxyadriamycinone in the presence of mercuric bromide/mercuric oxide with the above mentioned sugar halide. The new compounds of the invention are useful in treating certain tumors in mammals.

14 Claims, No Drawings

ANTHRACYCLINE GLYCOSIDES

BACKGROUND OF THE INVENTION

1. Field of the Invention

The present invention relates to a process for the preparation of anthracycline glycosides, to certain novel anthracycline glycosides thereby prepared, to pharmaceutical compositions containing said novel glycosides and the use thereof. The invention also relates to certain novel intermediates used in the preparation of the novel glycosides.

2. The Prior Art

The starting materials used in preparation of the compounds of the invention (daunomycinone and 4-demethoxy-daunomycinone) as well as the starting materials used in preparing the novel intermediates of the invention (adriamycinone and 4-demethoxy-adriamycinone) are all well known compounds described in the literature and in prior patents owned by the unrecorded assignee hereof.

SUMMARY OF THE INVENTION

The invention provides, in one aspect thereof, a process for the preparation of anthracycline glycosides having the formula I or formula II:

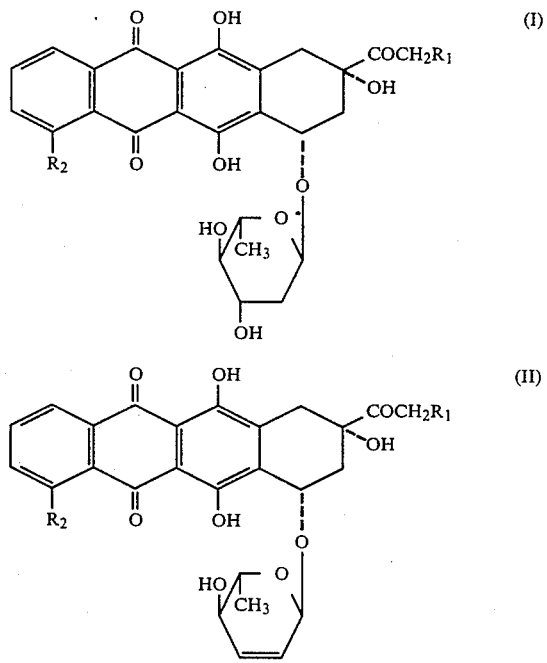

wherein $R_1$ is hydrogen or hydroxy and $R_2$ is hydrogen or methoxy. According to the process, an anthracyclinone of the formula III (below) wherein R is hydrogen or t-butyl-diphenyl-siloxy and $R_2$ is hydrogen or methoxy is condensed with 3,4-di-0-acetyl-2,6-dideoxy-α-L-arabino-hexopyranosyl chloride, which has the formula IV (below) and removing the acetyl protecting group(s) and, if necessary the t-butyl-diphenyl-silyl protecting group from the resultant anthracycline glycosides of the formula V and VI wherein R and $R_2$ are as defined above. The process is illustrated by the following reaction scheme:

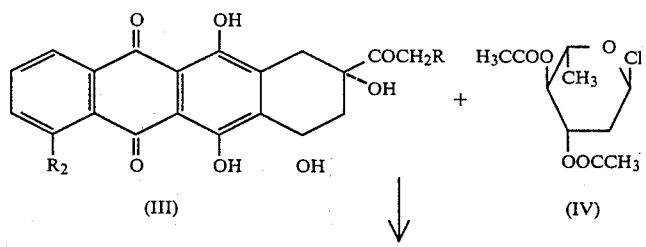

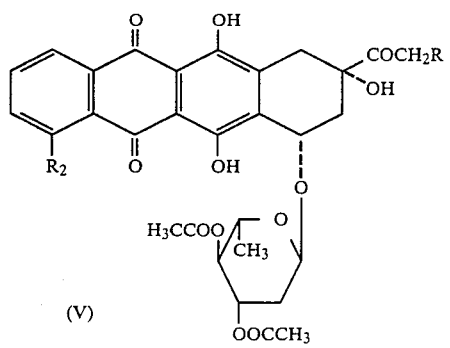

(V)

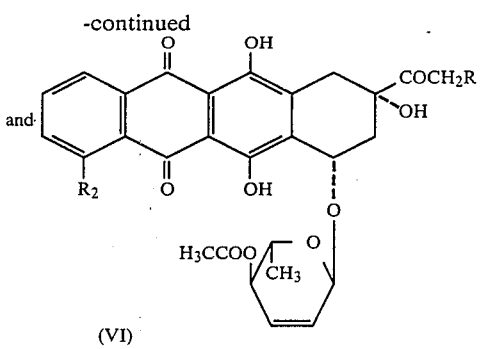

(VI)

| deprotection
↓
(I)

| deprotection
↓
(II)

The anthracyclinones III used as the starting materials for the process are the known compounds daunomycinone (III, R=H, $R_2$=CH$_3$O: hereinafter IIIa) and 4-demethoxy-daunomycinone (III, R=$R_2$=H: hereinafter IIIb) and the novel compounds 14-0-(t-butyl-diphenylsilyl)-adriamycinone (III, R=t-butyl-diphenyl-siloxy, $R_2$=CH$_3$O: hereinafter IIIc) and 14-0-(t-butyl-diphenyl-silyl)-4-demethoxy-adriamycinone (III, R=t-butyl-diphenyl-siloxy, $R_2$=H: hereinafter IIId).

The compounds IIIc and IIId, being novel are therefore also an aspect of the present invention. The compounds IIIc and IIId may be prepared by condensing the known compounds adriamycinone and 4-demethoxy-adriamycinone with t-butyl-diphenyl-chlorosilane in a solvent such as anhydrous dimethylformamide in the presence of an organic base such as imidazole. The t-butyl-diphenyl-silyl protecting group offers the advantages, as compared with other protecting groups, of remaining unaffected throughout the condensation and the removal of the acetyl protecting groups(s) and of being readily cleaved by treatment with tetra-n-butylammonium fluoride. The other starting material, the protected chloro-sugar IV, is also a known compound ( H. S. El Khadem et al., Carbohydr. Res. 58, 1977, 230).

The condensation may be effected under modified Koenigs-Knorr reaction conditions by dissolving the anthracylinone III in a solvent such as dichloromethane and reacting it with the chloro-sugar IV in a heterogeneous phase catalyzed by mercuric bromide and mercuric oxide or in a homogeneous phase catalyzed by silver trifluoromethanesulphonate. A mixture of glycosides V and VI is obtained. More particularly, the use of the anthracyclinone IIIa gives a mixture of the anthracycline glycosides V, R=H, $R_2$=CH$_3$O (hereinafter Va) and VI, R=H, $R_2$=CH$_3$O (hereinafter VIa); whereas the use of the anthracyclinone IIIb gives a mixture of the anthracycline glycosides V, R=$R_2$=H (hereinafter Vb) and VI, R=$R_2$=H (hereinafter VIb). Similarly, the use of the anthracyclinone IIIc gives a mixture of the anthracyclinone glycosides V, R=t-butyl-diphenyl-siloxy, $R_2$=CH$_3$O (hereinafter Vc) and VI, r=t-butyl-diphenyl-siloxy, $R_2$=CH$_3$O (hereinafter VIc); whereas the use of the anthracyclinone IIId gives a mixture of the anthracycline glycosides V, R=t-butyl-diphenyl-siloxy, $R_2$=H (hereinafter Vd) and VI, R=t-butyl-diphenyl-siloxy, $R_2$=H (hereinafter VId).

The respective anthracycline glycoside mixtures Va and VIa, Vb and VIb, Vc and VIc, and Vd and VId may be separated into their respective components by fractional crystallization or by chromatographic techniques.

Removal of the acetyl protecting group(s) by treatment with catalytic amounts of sodium methoxide in methanol or with aqueous sodium hydroxide solution, from Va, Vb, VIa and VIb gives, respectively, the anthracycline glycosides 7-0(2,6-dideoxy-α-L-arabino-hexopyranosyl)-daunomycinone (I, $R_1$=H, $R_2$=CH$_3$O: hereinafter Ia), 4-demethoxy-7-0-(2,6-dideoxy-α-L-arabino-hexopyranosyl)-daunomycinone (I, $R_1$=$R_2$=H: hereinafter Ib), 7-0-(2,3,6-trideoxy-α-L-erythro-hex-2-enopyranosyl)-daunomycinone (II, $R_1$=H, $R_2$=CH$_3$O: hereinafter IIa) and 4-demethoxy-7-0-(2,3,6-trideoxy-α-L-erythro-hex-2-enopyranosyl)-daunomycinone (II, $R_1$=$R_2$=H: hereinafter IIb).

Removal of the acetyl protecting group(s), as described above, followed by removal of the t-butyl-diphenyl-silyl protecting group by treatment with tetra-n-butyl-ammonium fluoride in tetrahydrofuran from Vc, Vd, VIc and VId gives, respectively, the anthracycline glycosides 7-0-(2,6-dideoxy-α-L-arabino-hex-opyranosyl)-adriamycinone (I, $R_1$=OH, $R_2$=CH$_3$O: hereinafter Ic), 4-demethoxy-7-0-(2,6-dideoxy-α-L-arabino-hexopyranosyl)-adriamycinone (I, $R_1$=OH, $R_2$=H: hereinafter Id), 7-0-(2,3,6-trideoxy-α-erythro-hex-2-enopyranosyl)-adriamycinone (II, $R_1$=OH, $R_2$=CH$_3$O: hereinafter IIc) and 4-demethoxy-7-0-(2,3,6-trideoxy-α-L-erythro-hex-2-enopyranosyl)-adriamycinone (II, $R_1$=OH, $R_2$=H: hereinafter IId).

The compounds Ia and Ic are known compounds which are described in British Patent Specification No. 8128252 owned by the unrecorded assignee hereof. The other anthracycline glycosides I and II, that is compounds Ib, Id, IIa, IIb, IIc and IId, are new compounds and are included within the scope of the invention. Accordingly, in another aspect thereof, the invention provides a new class of anthracycline glycoses of the formulae Ib, Id, IIa, IIb, IIc and IId. Like compounds Ia and Ic, the novel compounds according to the invention have properties useful in treating certain mammalian tumors, and the invention accordingly further provides pharmaceutical compositions comprising an anthracycline glycoside Ib, Id, IIb, IIc or IId in admixture with a pharmaceutically acceptable diluent or carrier therefor.

Finally, the invention provides methods of treating certain mammalian tumors by administration of the novel compounds of the invention.

DETAILED DESCRIPTION OF THE INVENTION

Example 1

Preparation of 14-O-(t-butyl-diphenyl-silyl)-adriamycinone (IIIc)

A solution of 0.414 g of adriamycinone in 20 ml of anhydrous dimethylformamide was treated with 0.28 ml of t-butyl-diphenyl-chloro-silane and 0.15 g of imidazole. The reaction mixture was left standing overnight at room temperature, after which 200 ml of water were added and the solution was extracted with methylene dichloride. The organic layer was separated off, dried over anhydrous sodium sulphate, filtered and evaporated to dryness under vacuum. The residue was then purified by chromatography on silica gel using the solvent mixture ethyl acetate:toluene (1:2 by volume) as eluting system. The pure IIIc (0.46 g) melts at 208°–209° C., FD-MS: m/z 652 (M+·)

PMR (CDCl$_3$): inter alia at 1.14$\delta$ (s, (CH$_3$)$_3$—C), 3.98$\delta$ (s, CH$_3$O) and 4.89 (s, CH$_2$—Si—).

Example 2

Preparation of 4-demethoxy-14-O-(t-butyl-diphenyl-silyl)-adriamycinone (IIId)

A solution of 0.385 g of 4-demethoxyadriamycinone in 15 ml of anhydrous dimethylformamide was treated with 0.3 ml of t-butyl-diphenyl-chloro-silane and 0.15 g of imidazole. The reaction mixture was left for 4 hours at room temperature, after which 200 ml water were added and the solution was extracted with methylene dichloride. The organic layer was separated off, dried over anhydrous sodium sulphate, filtered and evaporated to dryness under vacuum. The residue was then purified by chromatography on silica gel using the solvent mixture toluene: acetone (95:5 by volume) as eluting system. The pure IIId (0.6 g) melts at 101°–102° C. FD-MS: m/z 622 (M+·).

PMR (CDCl$_3$): inter alia at 1.13$\delta$ (s, (CH$_3$)$_3$, 3.41$\delta$ (d, OH-C-7), 4.87$\delta$ (s, CH$_2$—Si—), 5.24$\delta$ (m, C—H—7).

Example 3

Preparation of 7-O-(2,6-dideoxy-α-L-arabinohexopyranosyl)-daunomycinone (Ia) and 7-O-(2,3,6-trideoxy-α-L-erythro-hex-2-enopyranosyl-daunomycinone (IIa)

To a solution of 2 g of daunomycinone (IIIa) in 200 ml of anhydrous methylene dichloride were added 1.25 g of 3,4-di-O-acetyl-2,6-dideoxy-α-L-arabino-hexopyranosyl chloride (IV) dissolved in 30 ml of methylene dichloride in the presence of 12 g of molecular sieve (4Å Merck). The mixture was treated with 1.28 g of silver trifluoromethane sulphonate dissolved in 30 ml of anhydrous diethyl ether. After 5 minutes, the reaction mixture was neutralized with 0.65 ml of anhydrous collidine. After 30 minutes at room temperature the organic solution was washed with a saturated aqueous solution of sodium bicarbonate, water, aqueous 0.1N hydrochloric acid and finally with water. The organic phase was separated off and evaporated to dryness under vacuum. The resulting residue was purified by chromatography on a silicic acid column using ethyl acetate:cyclohexane (1:1 by volume) as the eluting system. There were obtained, separately, 0.9 g of product Va, m.p. 117°–118°, PMR (CDCl$_3$): inter alia at 1.23$\delta$ (d, CH$_3$—C—5'), 1.95$\delta$ (s, CH$_3$COOC), 2.07$\delta$ (s, CH$_3$COOC), 2.43$\delta$ (s, CH$_3$CO), 5.20$\delta$ (CH-7) and 5.53$\delta$ (CH-1'), and 0.9 g of product VIa, m.p. 83°–84°.

The compound Va (0.7 g) was dissolved in acetone (45 ml) and treated with 50 ml of 0.2N aqueous sodium hydroxide at room temperature. After one hour the solution was adjusted to pH 7 and extracted with chloroform. The evaporation of organic solvent under vacuum afforded pure Ia in quantitative yield: m.p. 161°–162° C., FD-MS: m/z 528 (M+·). Analogously the compound VIa after basic treatment under the above mentioned conditions afforded the pure IIa. m.p. 181°–182° C., FD-MS: m/z 510 (M+·), PMR (CDCl$_3$): inter alia at 1,40$\delta$ (d, CH$_3$—C—5'), 2.42$\delta$ (s, CH$_3$CO), 5.33$\delta$ (CH-7), 5.58$\delta$ (CH-1') and 5.5–6.0$\delta$ (m, CH-2'), CH-3').

Example 4

Preparation of 4-demethoxy-7-O-(2,6-dideoxy-α-L-arabino-hexopyranosyl)-daunomycinone (Ib) and 4-demethoxy-7-O-(2,3,6-trideoxy-α-L-erythro-hex-2-enopyranosyl)-daunomycinone (IIb)

To a solution of 0.74 g of 4-demethoxy-daunomycinone (IIIb) in anhydrous methylene dichloride (70 ml) were added 0.65 g of the halosugar IV in 10 ml of methylene dichloride in the presence of 5 g of molecular sieve (4Å Merck). The mixture was treated with 0.64 g of silver trifluoromethane sulphonate and dissolved in 15 ml of anhydrous diethyl ether. After 5 minutes the reaction mixture was neutralized with 0.4 ml of anhydrous collidine. After 1 hour at room temperature the organic solution was washed with a saturated aqueous solution of sodium bicarbonate, water, aqueous 0.1N hydrochloric acid, and finally with water. The organic phase was separated off and evaporated to dryness under vacuum. The resulting residue was purified by chromatography on a silicic acid column using chloroform: acetone (96:4 by volume) as the eluting system. There were obtained 0.48 g of product Vb, m.p. 65°–66° C. FD-MS: m/z 582 (M+·), and 0.45 g of product VIb. The compound Vb was dissolved in 20 ml of acetone and treated with 20 ml of 0.2N aqueous sodium hydroxide at room temperature. After 1 hour the solution was adjusted to pH 7 and extracted with chloroform. Evaporation of the organic solvent under vacuum afforded pure Ib in quantitative yield: m.p. 165°–166° C., FD-MS: m/z 498 (M+·). Analogously the compound VIb after basic treatment under the above mentioned conditions afforded pure IIb. PMR (CDCl$_3$) inter alia at 1.39 (CH$_3$—C—5'), 2.42$\delta$ (s, CH$_3$-CO), 3,50–4,00$\delta$ (m, C-H-4' and C-H-5'), 4,08$\delta$ (s, CH$_3$O), 5.33$\delta$ (bs, C-H-7), 5.58$\delta$ (bs, C-H-1'), 5.65 (d, C-H-3'), 5.93$\delta$ (d, C-H-2').

Example 5

Preparation of 7-O-(2,6-dideoxy-α-L-arabinohexopyranosyl)-adriamycinone (Ic) and 7-O-(2,3,6-trideoxy-α-L-erythro-hex-2-enopyranosyl)-adriamycinone (IIc)

To a solution of 1.25 g of IIIc, prepared as described in Example 1, in 100 ml of anhydrous methylene dichloride were added 2.4 g of mercuric oxide, 0.75 g of mercuric bromide, 8 g of molecular sieve (4Å Merck) and 0.85 g of the chlorosugar IV. The mixture was stirred at room temperature overnight and then filtered. The filtrate was evaporated to dryness under vacuum to yield a residue, which was purified by chromatography on a silicic acid column using toluene:acetone (9:1 by volume) as the eluting system. There were obtained 1.2 g of product Vc: m.p. 55°–56° C., FD-MS: m/z 866 (M+·), and 0.15 g of product VIc: m.p. 88°–89° C. The compound Vc (0.87 g) was dissolved in anhydrous methylene dichloride (10 ml) and treated with 200 ml of a 0.01N solution of sodium methoxide in anhydrous methanol. After three hours at room temperature the acetyl protecting groups had been removed. The reaction mixture was acidified with acetic acid and evaporated under vacuum. The obtained oil was dissolved in 200 ml of tetrahydrofuran and treated with 0.7 g of tetra-n-butylammonium fluoride. After 1.5 hours the hydrolysis of the t-butyl-diphenyl-silyl group was complete. The residue obtained by evaporating off the solvent under vacuum was purified by chromatography on a column of silica gel using toluene:acetone (1:1 by volume) as the eluting system to afford pure Ic (0.35 g); m.p. 189°–190° C., PMR (CDCl$_3$) inter alia: at 1.34$\delta$ (d, CH$_3$-C-5'), 0.08$\delta$ (s, CH$_3$O), 4.77$\delta$ (s, CH$_2$OH), 5.30$\delta$ (d, CH-7), 5.50$\delta$ (d, CH-1').

Analogously the compound VIc by hydrolysis of the protecting groups gave IIc; m.p. 205°–207° C., PMR (CDCl$_3$) inter alia: at 1.38$\delta$ (d, CH$_3$-C-5'), 3.25–4.00$\delta$ (m, C-H-4' and C-H-5'), 4.08$\delta$ (s, CH$_3$O), 4.76$\delta$ (d, CH$_2$OH), 5.36$\delta$ (broad s, C-H-7), 5.57$\delta$ (broad s, C-H1'), 5.63$\delta$ (d, C-H-3'), 5.93$\delta$ (d, C-H-2').

Example 6

Preparation of
4-demethoxy-7-0-(2,6-dideoxy-α-L-arabino-hexopyranosyl)-adriamycinone (Id) and
4-demethoxy-7-0-(2,3,6-trideoxy-α-L-erythro-hex-2-enopyranosyl)-adriamycinone (IId)

To a solution of 0.63 g of IIId, prepared as described in Example 2, in 50 ml of anhydrous methylene dichloride were added 1.2 g of mercuric oxide, 0.4 g of mercuric bromide, 8 g of molecular sieve (4Å Merck) and 0.75 g of the chlorosugar IV. The mixture was stirred at room temperature overnight and the filtered. The filtrate was evaporated under vacuum to yield a residue, which was purified by chromatography on a silicic acid column using toluene:acetone (96:4 by volume) as the eluting system. There were obtained 0.585 g of product Vd, m.p. 212°–213°, FD-MS: m/z 236 (M+·) and 0.200 g of product VId. The product Vd (0.5 g) was dissolved in anhydrous methylene dichloride (10 ml) and treated with 150 ml of an 0.01N solution of sodium methoxide in anhydrous methanol. After three hours at room temperature the removal of the acetyl protecting groups was complete. The reaction mixture was acidified with acetic acid and evaporated to dryness under vacuum. The residue was dissolved in 100 ml of tetrahydrofuran and treated with 0.5 g of tetra-n-butyl-ammonium fluoride. After 2 hours the hydrolysis of the t-butyl-diphenyl-silyl group was complete. The residue obtained by evaporating off the solvent under vacuum was purified by chromatography on a column of silica gel using toluene:acetone (1:1 by volume) as the eluting system to afford 0.2 g of pure Id, m.p. 204°–206° C., FD-MS m/z 514 (M+·), PMR CDCl$_3$): inter alia at 1.3$\delta$ (d, CH$_3$-C-5'), 4.78$\delta$ (s, CH$_2$OH), 5.34$\delta$ (broad s, CH-7), 5.54$\delta$ (bs, C-H-1'). Analogously the compound VId by hydrolysis of the protecting groups gave IId, m.p. 166°–167° C., PMR (CDCl$_3$): inter alia at 1.39$\delta$ (d, CH$_3$-C-5'), 3.96$\delta$ (d, C-H4'), 4.77$\delta$ (s, CH$_2$OH), 5.35$\delta$ (broad s, C-H-7), 5.55$\delta$ (broad s, C-H-1'), 5.71$\delta$ (m, CH-3'), 5.95$\delta$ (d, C-H-2').

BIOLOGICAL ACTIVITY OF COMPOUNDS IIa, Ib, IIc and Id

The compounds IIa and IIc were tested in comparison with daunorubicin (DNR) and doxorubicin (DX) respectively in "in vitro" and "in vivo" systems in order to ascertain their cytotoxicity and antitumor activity.

Table 1 summarizes the effect of HeLa cells cloning efficiency "in vitro". IIa is about 25 times less cytotoxic than DNR and IIc is about 5 times less cytotoxic than DX.

The primary screening "in vitro" was carried out in CDF-1 mice bearing ascitic P388 leukemia (10$^6$ cells/mouse). Results are reported in Table 2. Both IIa and IIc were suspended in 10%. Tween 80 and injected intraperitoneally. The two compounds are less toxic and potent than the parent drugs DNR and DX. IIa was inactive on the P388 ascitic leukemia at the two doses tested, including the Maximal Tolerated Dose (Mx TD) of 100 mg/kg, while IIc was found to have a certain antitumor activity, which is lower than that of DX.

Compounds Ib and Id were studied "in vitro" on HeLa and P388 leukemia cells sensitive (P388) and resistant (P388/DX) to DX and "in vitro" on P388 and Gross leukemia. Data reported in Table 3 shows that Ib tested on HeLa cells cloning efficiency "in vitro" in comparison to the parent compounds DNR and 4-demethoxy DNR (4-dm DNR) is 3 and 6 times less cytotoxic than DNR and 4-dm DNR respectively, while Id is as cytotoxic as DX in the same test.

Compound Ib was studied on P388/DX "in vitro".

P388 and P388/DX leukemia cells were harvested from mice ascitic fluid and adapted to grow in suspension "in vitro". Cytotoxicity tests were carried out exposing the cells to various drug concentrations for 48 hrs; at the end of the exposure period, cells were counted with a coulter cell counter, and the ID$_{50}$ (dose which gives 50% reduction of the cell number in comparison with untreated controls) was calculated.

Table 4 shows that Ib was about as cytotoxic as DNR on P388 leukemia cells and was very active on P388/DX leukemia cells. DNR was about 500 fold less active on the resistant than on the sensitive line.

Results of the primary screening "in vivo" carried out in CDF-1 mice bearing P388 ascitic leukemia and treated i.p. the day after tumor transplantation, are reported in Table 5.

Ib was 2 times more potent than DNR and about 1.5 times less potent than 4-dm DNR; comparison at the Mx TD shows that the compound is less active than DNR and 4-dm DNR. Compound Id was about 5 times more potent than DX. The antileukemia activity against P388 leukemia was good but lower than that of DX.

Results of studies performed in C3H/Me mice carrying i.v. transplanted Gross leukemia and treated i.v. the day after tumor transplantation, are reported in Table 6. Both Ib and Id are more toxic and more potent than the parent compounds. Comparison of the Mx TD shows that Ib is more active than DNR and Id has a good antitumor activity, which is of the same order of magnitude as that of DX. The compounds Ib and Id were further investigated for oral activity on Gross leukemic transplanted i.v., in comparison with DNR, DX given i.v. and 4-dm DNR given oral route.

Data reported in Table 7 shows that Ib has a good antitumor activity when given orally at day 1, comparable to that of 4-dm DNR (already demonstrated to be active by oral route) and DNR injected i.v.

Data on antitumor activity of Id given orally at day 1 or 1,2,3 after tumor transplantation are also reported in Table 7.

When given orally at day 1, Id at the Mx TD was less active than DX i.v. However with a different schedule of treatment (1,2,3) the antitumor activity of the compound was higher than that of DX given i.v.

TABLE 1

Colony inhibition test against HeLa cells "in vitro" (treatment for 24 hrs).

| Compound | Dose (ng/ml) | %[a] | ID$_{50}$ (ng/ml) |
|---|---|---|---|
| DNR | 25 | 12 | |
| | 12.5 | 74 | ~16 |
| | 6.2 | 106 | |
| Compound IIa | 400 | 146 | |
| | 100 | 136 | 400 |
| | 25 | 143 | |
| | 6.2 | 127 | |
| | 1.5 | 120 | |
| DX | 25 | 24 | ~10 |
| | 12.5 | 40 | |
| | 6.2 | 69 | |
| Compound IIc | 400 | 4 | |
| | 100 | 33 | ~50 |
| | 25 | 65 | |
| | 6.2 | 68 | |
| | 1.5 | 86 | |

[a]No of colonies; % of untreated controls.

TABLE 2

Antitumor activity against ascitic P388 leukekemia. Treatment i.p. on day 1.

| Compound | Dose (mg/kg) | T/C[a] % | LTS[b] | Toxic deaths[c] |
|---|---|---|---|---|
| DNR | 2.9 | 160 | 0/10 | 0/10 |
| | 4.4[d] | 165–170 | 0/10 | 0/20 |
| | 6.6[d] | 150–160 | 0/10 | 7/20 |
| Compound IIa | 75 | 120 | 0/5 | 0/5 |
| | 100 | 90 | 0/10 | 1/10 |
| DX | 4.4[d] | 220–227 | 2/18 | 0/18 |
| | 6.6[e] | 227–305 | 2/26 | 0/26 |
| | 10[e] | 268–>610 | 7/26 | 3/26 |
| Compound IIc | 17.6 | 118 | 0/8 | 0/8 |
| | 23 | 127 | 0/7 | 0/7 |
| | 30[d] | 125–136 | 0/17 | 0/17 |
| | 45 | 130 | 0/10 | 0/10 |
| | 67.5 | 140 | 0/10 | 0/10 |
| | 100 | 150 | 0/7 | 0/7 |

[a]median survival time; % over untreated controls
[b]long term survivors ($\geq$60 days)
[c]evaluated on the basis of autoptic findings on dead mice
[d]data of two experiments (range)
[e]date of three experiments (range)

TABLE 3

Colony inhibition test against HeLa cells "in vitro" (treatment for 24 hrs).

| Compound | Dose (ng/ml) | %[a] | ID$_{50}$ (ng/ml) |
|---|---|---|---|
| DNR | 25 | 9 | |
| | 12.5 | 51 | ~12 |
| | 6.2 | 83 | |
| 4-dm DNR | 25 | 0 | |
| | 12.5 | 18 | ~6.3 |
| | 6.2 | 53 | |
| | 3.1 | 84 | |
| Compound Ib | 100 | 0 | |

TABLE 3-continued

Colony inhibition test against HeLa cells "in vitro" (treatment for 24 hrs).

| Compound | Dose (ng/ml) | %[a] | ID$_{50}$ (ng/ml) |
|---|---|---|---|
| | 25 | 67 | ~35 |
| | 6.2 | 87 | |
| | 1.5 | 107 | |
| DX | 25 | 0 | |
| | 12.5 | 28 | ~7.5 |
| | 6.2 | 59 | |
| Compound Id | 100 | 0 | |
| | 25 | 0 | ~7. |
| | 6.2 | 59 | |
| | 1.5 | 106 | |

[a]No of colonies; % of untreated controls.

TABLE 4

Effect on sensitive and doxorubicin-resistant P388 leukemia "in vitro"

| Compound | ID$_{50}$ (ng/ml)[a] | | R[d] |
|---|---|---|---|
| | P388[b] | P388/DX[e] | |
| DNR | 1.7 | 800 | 470 |
| Compound Ib | 1.2 | 30 | 25 |

[a]Dose giving 50% reduction of cell number in comparison with untreated controls
[b]P388 leukemia cells sensitive to DX
[c]P388 leukemia cells resistant to DX
[d]Ratio between ID$_{50}$ on P388/DX and ID$_{50}$ on P388

TABLE 5

Antitumor activity of Ib and Id against ascitic P388 leukemia. Treatment i.p. on day 1.

| Compound | Dose (mg/kg) | T/C[a] % | LTS[b] | Toxic deaths[c] |
|---|---|---|---|---|
| DNR | 2.9[d] | 159–194 | 0/18 | 0/8 |
| | 4.4[d] | 140–184 | 0/18 | 7/18 |
| 4-dm DNR | 0.75 | 163 | 0/8 | 0/8 |
| Compound Ib | 1.25 | 140 | 0/8 | 0/8 |
| | 2.5 | 163 | 0/9 | 3/9 |
| | 5 | 63 | 0/10 | 10/10 |
| DX | 4.4 | 220 | 1/10 | 0/10 |
| | 6.6 | 305 | 0/10 | 0/10 |
| | 10 | >610 | 5/10 | 0/10 |
| Compound Id | 1.12 | 170 | 0/10 | 0/10 |
| | 1.68 | 185 | 0/10 | 0/10 |
| | 2.53 | 230 | 1/10 | 2/10 |

[a,b,c,d]see Table 2.

TABLE 6

Antitumor activity against i.v. Gross leukemia. Treatment i.v. on day 1.

| Compound | Dose (mg/kg) | T/C[a] % | Toxic deaths[b] |
|---|---|---|---|
| DNR | 15 | 171 | 0/8 |
| | 22.5 | 171 | 0/8 |
| Compound Ib | 2.9 | 214 | 0/7 |
| | 4.4 | 100 | 7/8 |
| DX | 10 | 171 | 0/10 |
| | 13 | 200 | 0/10 |
| | 16.9 | 207 | 3/10 |
| Compound Id | 1.2 | 171 | 1/10 |
| | 2.16 | 200 | 1/10 |
| | 3.8 | 114 | 5/9 |

[a,b]See Table 2.

TABLE 7

Oral activity of Ib and Id against Gross leukemia

| Route | Treatment schedule[a] | compound | dose (mg/kg) | T/C %[b] | Toxic deaths[c] |
|---|---|---|---|---|---|
| i.v. | +1 | DNR | 15 | 200 | 0/10 |

TABLE 7-continued

Oral activity of Ib and Id against Gross leukemia

| Route | Treatment schedule[a] | compound | dose (mg/kg) | T/C %[b] | Toxic deaths[c] |
|---|---|---|---|---|---|
|  |  |  | 22.5 | 125 | 6/10 |
| Oral | +1 | 4-dm DNR | 3 | 150 | 0/6 |
|  |  |  | 3.6 | 150 | 0/6 |
|  |  |  | 4.3 | 216 | 0/3 |
| Oral | +1 | Compound Ib | 2.9 | 167 | 0/10 |
|  |  |  | 4.4 | 208 | 0/10 |
|  |  |  | 6.6 | 116 | 4/9 |
| i.v. | +1 | DX | 10[d] | 171–171 | 1/20 |
|  |  |  | 13[d] | 200–200 | 1/20 |
|  |  |  | 16.9[d] | 200–207 | 3/13 |
| Oral | +1 | Compound Id | 1.2 | 171 | 0/9 |
|  |  |  | 2.1 | 185 | 0/8 |
|  |  |  | 3.8 | 214 | 3/8 |
| Oral | 1,2,3 | Compound Id | 0.48 | 183 | 0/10 |
|  |  |  | 0.62 | 208 | 0/10 |
|  |  |  | 0.8[d] | 233–258 | 2/20 |

[a]days after transplantation
[b,c]see Table 2
[d]data of two experiments (range)

What is claimed is:

1. An anthracycline glycosidic compound of the formula I:

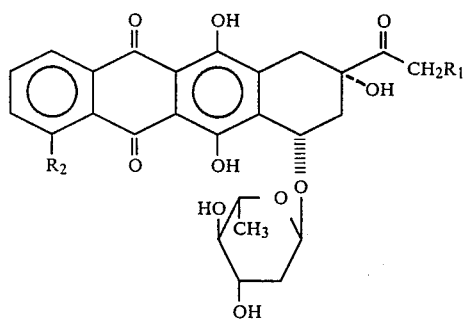

wherein $R_1$ is hydrogen or hydroxy and $R_2$ is hydrogen.

2. An anthracycline glycosidic compound of the formula II:

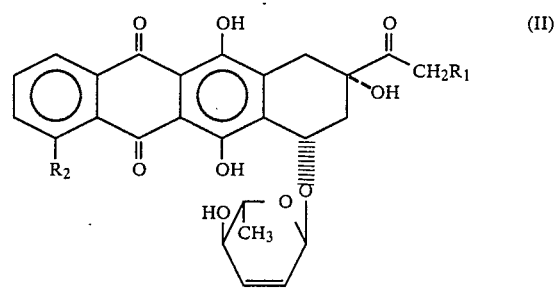

wherein $R_1$ is hydrogen or hydroxy and $R_2$ is hydrogen or methoxy.

3. A compound according to claim 1 which is 4-demethoxy-7-0-(2,6-dideoxy-α-L-arabino-hexopyranosyl-daunomycinone.

4. A compound according to claim 1 which is 4-demethoxy-7-0-(2,6-dideoxy-α-L-arabino-hexopyranosyl)-adriamycinone.

5. A compound according to claim 2 which is 7-0-(2,3,6-trideoxy-α-L-erythro-hex-2-enopyranosyl)-daunomycinone.

6. A compound according to claim 2 which is 4-demethoxy-7-0-(2,3,6-trideoxy-α-L-erythro-hex-2-enopyranosyl-daunomycinone.

7. A compound according to claim 2 which is 7-0-(2,3,6-trideoxy-α-L-erythro-hex-2-enopyranosyl)-adriamycinone.

8. A compound according to claim 2 which is 4-demethoxy-7-0-(2,3,6-trideoxy-α-L-erythro-hex-2-enopyranosyl)-adriamycinone.

9. A pharmaceutical composition for inhibiting the growth of P388 leukemia or transplanted gross leukemia comprising a therapeutically effective amount of an anthracycline glycoside according to claim 1.

10. A method of inhibiting the growth of P388 leukemia or transplanted gross leukemia comprising administering to a mammal afflicted therewith, a therapeutically effective amount of an anthracycline glycoside according to claim 1.

11. A method according to claim 10 wherein the anthracycline glycoside is administered intraperitoneally, intravenously or orally.

12. A pharmaceutical composition for inhibiting the growth of P388 leukemia or transplanted gross leukemia comprising a therapeutically effective amount of an anthracycline glycoside according to claim 2.

13. A method of inhibiting the growth of P388 leukemia or transplanted gross leukemia comprising administering to a mammal afflicted therewith, a therapeutically effective amount of an anthracycline glycoside according to claim 2.

14. A method according to claim 13 wherein the anthracycline glycoside is administered intraperitoneally, intravenously or orally.

* * * * *